United States Patent
Fischell et al.

[11] Patent Number: 6,006,124
[45] Date of Patent: Dec. 21, 1999

[54] MEANS AND METHOD FOR THE PLACEMENT OF BRAIN ELECTRODES

[75] Inventors: Robert E. Fischell, Dayton; Richard B. North, Baltimore, both of Md.

[73] Assignee: NeuroPace, Inc., Fair Haven, N.J.

[21] Appl. No.: 09/071,055

[22] Filed: May 1, 1998

[51] Int. Cl.[6] .............................. A61B 5/04; A61N 1/05
[52] U.S. Cl. .......................................... 600/378; 607/116
[58] Field of Search ................................. 600/377, 378; 604/175; 606/129, 130; 607/116, 139

[56] References Cited

U.S. PATENT DOCUMENTS

| | | | |
|---|---|---|---|
| 3,850,161 | 11/1974 | Liss | 128/2.1 R |
| 3,918,461 | 11/1975 | Cooper | 128/422 |
| 4,245,645 | 1/1981 | Arseneault et al. | 600/378 |
| 4,702,254 | 10/1987 | Zabara | 128/421 |
| 5,299,569 | 4/1994 | Wernike et al. | 607/405 |
| 5,843,150 | 12/1998 | Dreessen et al. | 604/175 |
| 5,865,842 | 2/1999 | Knuth et al. | 607/116 |

Primary Examiner—Lee Cohen

[57] ABSTRACT

Disclosed are a means and a method for the placement of insulated electrical wires beneath the human scalp in such a way that they will experience no flexing after implantation thus disallowing wire breakage. Specifically, this intracranial system uses wires to connect a control module containing various electronic systems to brain electrodes. These wires are placed in grooves that are made by a surgeon in an outer portion of the patient's cranium by means of a specially shaped burr rotated at high speed by means of a router. At the end of the groove, the surgeon would drill a burr hole in the cranium at the site where a brain electrode is to be placed. A distal portion of each electrical wire would be in the form of a helical coil; one helical coil would be placed in each burr hole. The grooves and burr holes could be filled with an adhesive filler type of material to form a smooth outer surface for the cranium. Also, a special cap could be placed over the burr hole. The function of the cap would be to form a smooth outer surface for the cranium. The electrodes at the end of the wires could be placed at various locations such as deep into the brain, on the brain surface, or in close proximity to the brain.

11 Claims, 4 Drawing Sheets

MEANS AND METHOD FOR THE PLACEMENT OF BRAIN ELECTRODES

FIELD OF USE

This invention is in the field of devices and methods for the placement of electrodes into, on, or in close proximity to the brain of a human subject.

BACKGROUND

Electrodes are often placed in close proximity to the brain or deep into the brain structures. Wires to connect these brain electrodes to amplifiers, stimulators or other electronic equipment typically are placed through the patient's skin or scalp. It is conceived that intracranial systems will become available in the near future for the treatment of various neurological disorders that originate in the brain. It is therefore important to be able to provide electrical wire connections to such electrodes without subjecting such wires to frequent bending that might lead to wire breakage.

SUMMARY OF THE INVENTION

Described herein are a means and a method for the placement of insulated electrical wires beneath the human scalp in such a way that they will experience no flexing after implantation thus disallowing wire breakage. Specifically, this intracranial system uses wires to connect a control module containing various electronic systems to brain electrodes. These wires are placed in grooves that are made by a surgeon in an outer portion of the patient's cranium by means of a specially shaped burr rotated at high speed by means of a router. The router removes cranium bone to form an elongated groove in the cranium thereby providing a fixed channel for placing a wire to connect the control module to a brain electrode.

At the end of the groove, the surgeon would drill a burr hole in the cranium at the site where a brain electrode is to be placed. The diameter of the burr hole would be approximately one to two centimeters. Within the burr hole the wire is formed into a helical shape. The purpose of the considerable wire length in the helix is to allow a fixed length of electrical wire from the control module to the electrode that can be used for electrode placement at various distances from the control module. For example, if a first electrode is placed 3 centimeters from the control module, the 3 centimeters of a 15-centimeter long wire would lie in the groove formed by the router and 12 centimeters of wire length would be within the helix in the burr hole. The same 15 centimeters length of wire could be used to reach an electrode placed 10 centimeters from the control module if 10 centimeters was placed in the router formed groove and 5 centimeters of wire length would be within the helix in the burr hole. Thus all the electrodes and connecting wires could be formed in manufacturing and the surgeon would not have to cut various lengths of the connecting wires during surgical implantation of the system.

The electrodes at the end of the wires could be placed in various locations such as: (1) on top of the cranium, (2) inside the burr hole, (3) between the bottom of the cranium and the dura mater, (4) between the dura mater and the arachnoid, (5) subdural on the brain's surface, or (6) separate depth electrodes could be placed deep into the brain. Any of these electrodes will be referenced to herein as "brain electrodes".

The grooves and burr holes could be filled with an adhesive or filler type of material such as bone wax to form a smooth outer surface for the cranium. Also, a special cap could be placed over the burr hole. The function of the cap would be to form a smooth outer surface for the cranium.

Thus, an object of this invention is to form grooves into the outer portion of the cranium and place electrical wires in the groove.

Another object of the invention is to have a connecting wire that has a distal portion which is in the shape of a helical coil, which coil can be placed in a burr hole.

Still another object of this invention is to have a control module and a multiplicity of electrical wires each connected to an electrode, each of the wires bring of a fixed length.

Still another object of this invention is to place an adhesive or filler substance over the wires placed in grooves in the cranium to make a smooth outer surface of the cranium.

Still another object of this invention is to have a burr hole cap that forms a covering for a burr hole that provides a smooth outer surface for the cranium.

Still another object of this invention is to have a router with a special bit and depth limiting means for forming a groove of an exact depth in an outer portion of the cranium.

Thus it is an object of this invention to have at least one brain surface electrode and/or at least one deep brain electrode and/or the electrical conducting case of an electronics control module that cooperate to provide an electrical current between two electrodes so as to depolarize the brain tissue that lies between the at least two electrodes.

These and other objects and advantages of this invention will become apparent to a person of ordinary skill in this art upon careful reading of the detailed description of this invention including the drawings as presented herein.

DETAILED DESCRIPTION OF THE INVENTION

Figure 1:
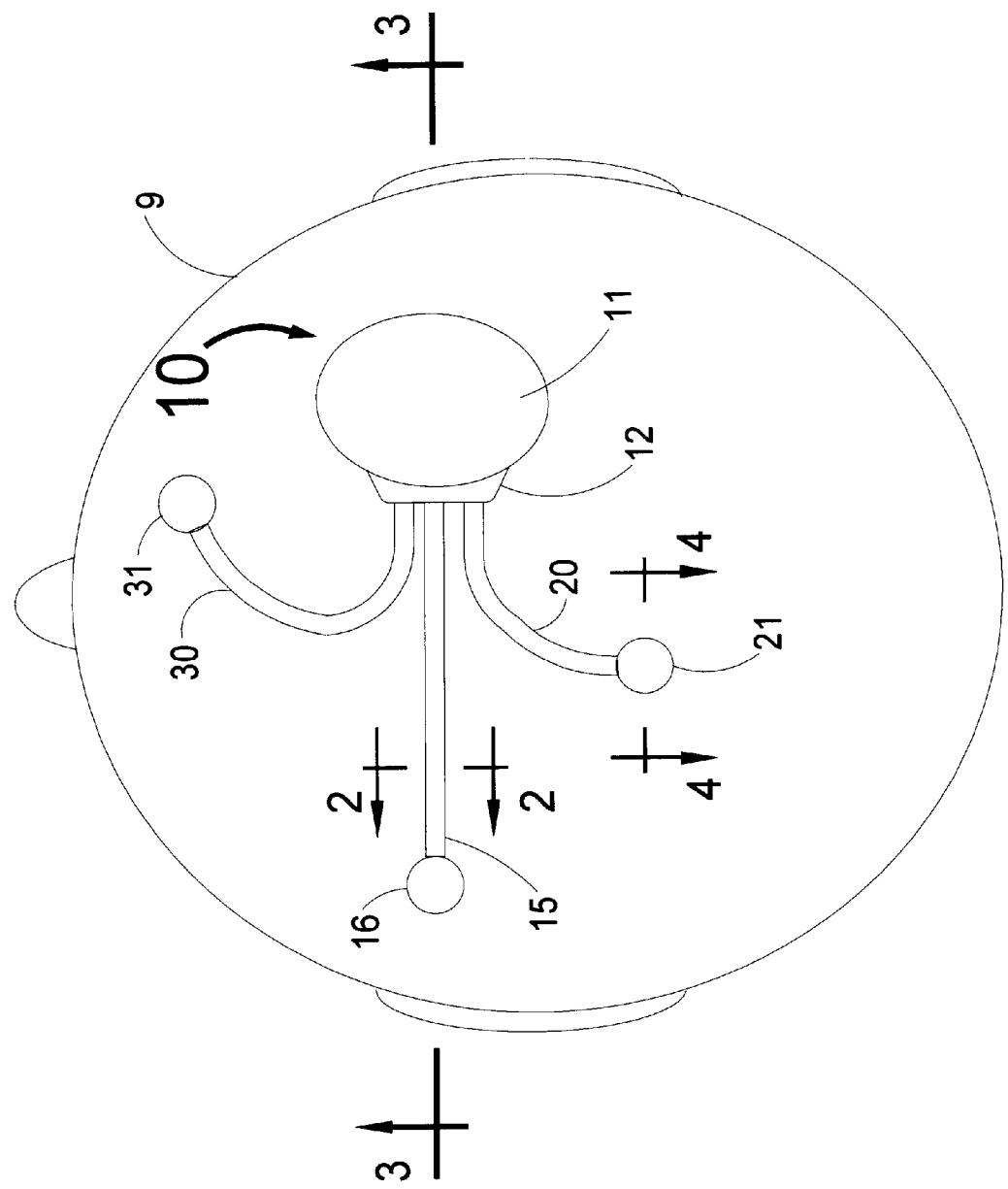
FIG. 1 is a top view of a cranium of a human subject with the scalp removed showing the placement of a control module, burr hole caps and electrical connecting wires.

FIG. 1 is a top view of the intracranial system 10 placed in the cranium of a human subject. The system 10 includes a control module 11 having a strain relief section 12 and electrical connecting wires 15, 20 and 30. The system 10 also includes burr hole caps 16, 21 and 31 which cover burr holes made in the cranium as seen in FIGS. 3 and 4.

The control module 11 of FIG. 1 would typically contain electronic circuitry used for the treatment, detection and/or recording of neurological events such as epileptic seizures. The control module 11 would also typically contain a battery and circuitry for two-way communication with externally located equipment.

Figure 2:
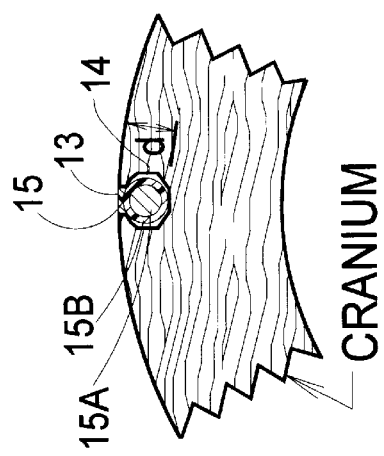
FIG. 2 is an enlarged cross section of the cranium taken at section 2–2 of FIG. 1 showing a router formed groove in an upper portion of the cranium.

FIG. 2 is a highly enlarged cross section of the cranium showing the groove 14 that is cut to a depth "d" in an outer portion of the cranium into which the wire 15 has been placed. An adhesive type of filler material 13 (such as methyl methacrylate) could be placed into the groove 14 after the wire 15 has been placed in the groove 14 to provide a smooth outer surface for the cranium. The wire 15 has an electrically conducting core 15A and insulation 15B.

Figure 3:
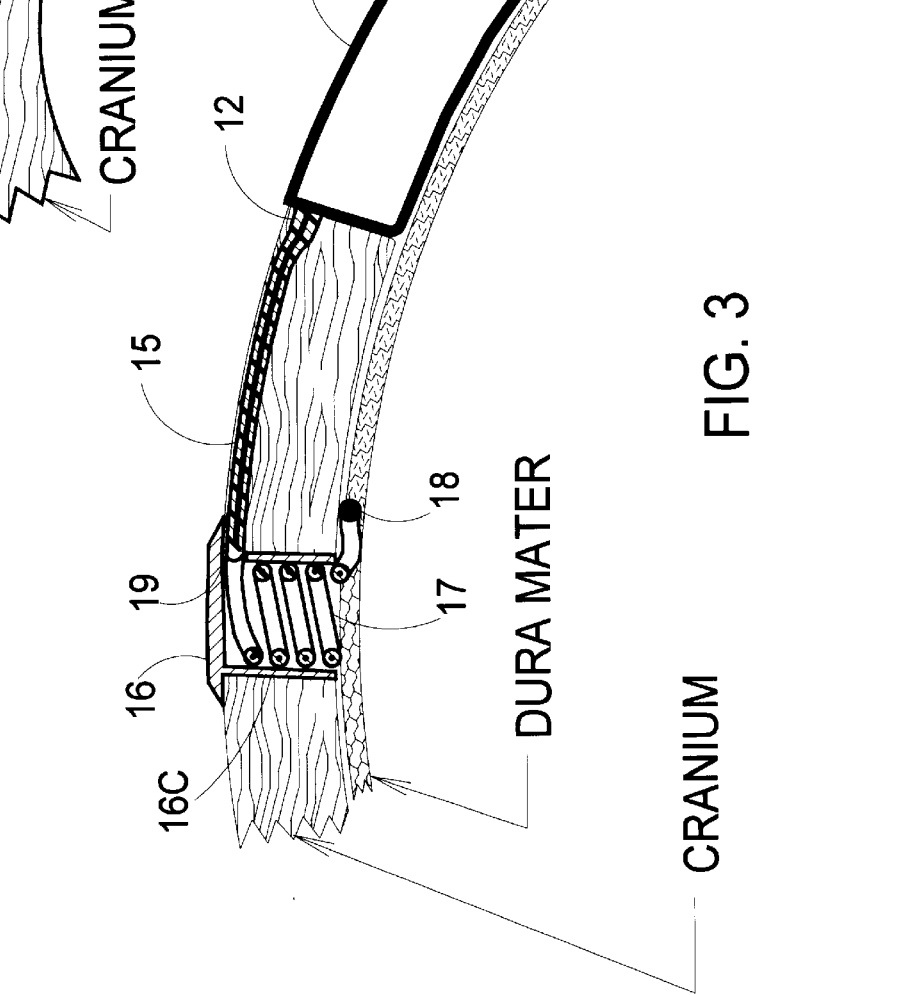
FIG. 3 is a cross section of the cranium at section 3—3 of FIG. 1 showing the placement of the control module, a connecting wire, an electrode and a burr hole cap.
Figure 4:
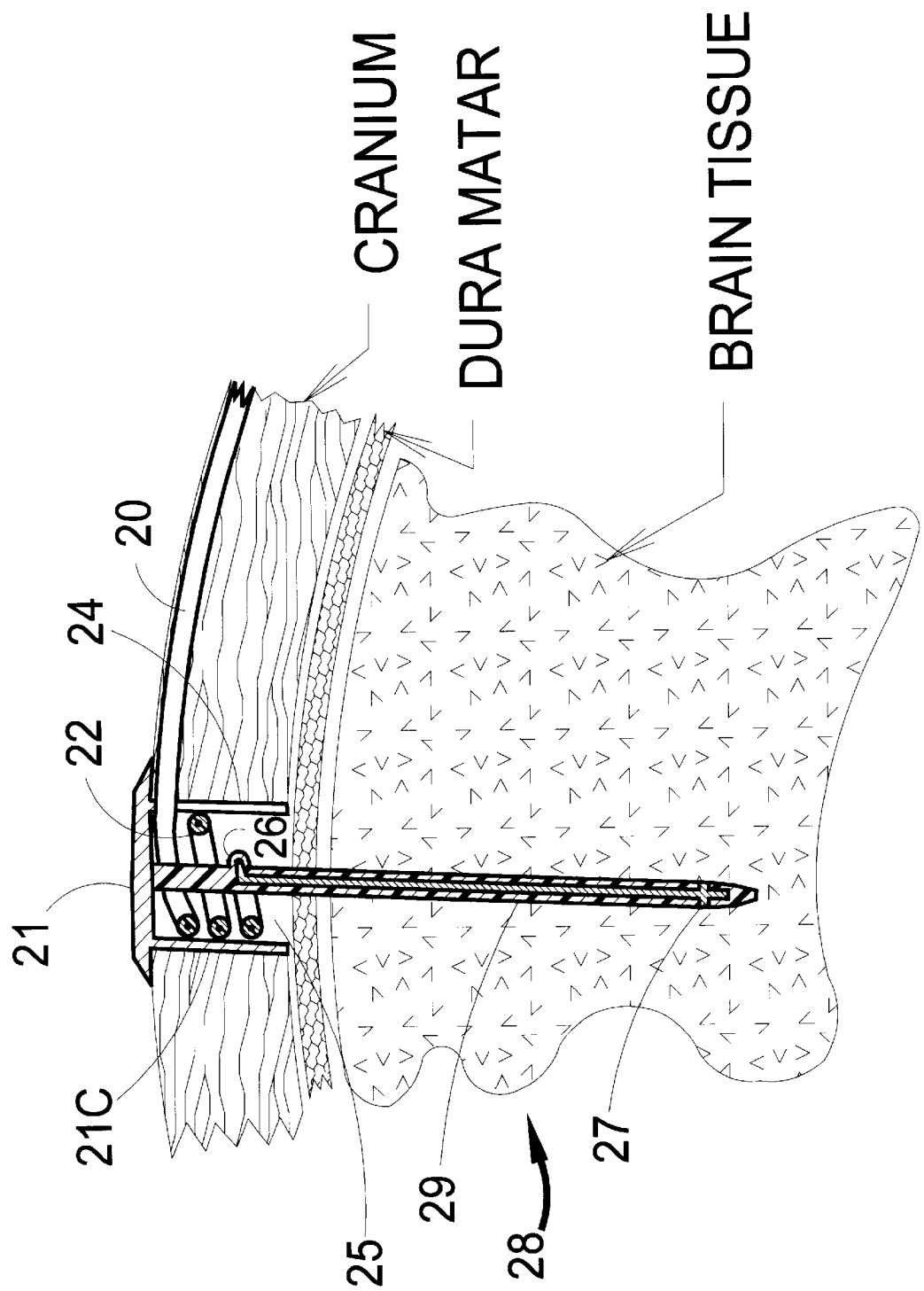
FIG. 4 is an enlarged cross section of the cranium at section 4—4 of FIG. 1 showing the placement of a deep brain electrode.

FIG. 3 is a cross section of the cranium showing the control module 11, strain relief section 12, wire 15, and burr hole cap 16. As seen in FIG. 3, a distal portion of the wire 15 is in the form of a helix 17 that has been placed in a burr hole that has been formed in the cranium. Most of the length of wire 15 could be preformed into a helical shape. The portion of the wire 15 placed in the groove would be automatically straightened when placed in the groove. The length of the wire 15 that is not placed in a groove would be placed in a burr hole having a diameter between a 0.5 and a 2.5-centimeters. Within the burr hole, the wire would form into its preformed shape that is the helix 17. The helix 17 would have an electrode 18 placed at its distal end.

By this construction, a wire whose length was fixed in manufacturing could be used to reach essentially any location for a brain electrode without requiring the surgeon to shorten the wire or splice an additional length of wire during surgical implantation. Thus, a wire that had a straightened length of, let us say, 20 centimeters, could be used to reach any desired location for placement of a brain electrode. It may be desired to have, let us say, 6 wires each with a length of 20 centimeters, or 3 with a length of 20 centimeters and 3 with a length of 12 centimeters; or any other logical combination of fixed lengths for the wires when straightened.

The burr hole cap 16 shown in FIG. 3 would have a side hole 19 through which the helix 17 of the wire 15 could be placed. The cylindrical portion 16C of the burr hole cap 16 could have an elongated slot (shown in FIG. 4) that would allow the electrode 18 to be placed before placing the burr hole cap 16 into the burr hole in the cranium.

FIG. 4 shows a deep brain electrode 28 which is joined by an electrical connector 26 to the distal end of the helical coil 22, which helical coil 22 forms the distal portion of the wire 20 (see FIG. 1). The deep brain electrode 28 has an exposed metal surface 27 and insulated covering 29. It is further envisioned that the deep electrode 28 could in fact be bipolar with two helical coils in the burr hole 25 and bipolar electrodes situated along the length of the insulated covering 29. Still further, two or more helical coils 22 could be placed in each burr hole 25 and a multiplicity of electrodes could emerge from the insulated covering 29.

It can be seen in FIG. 4 that the wire 20 enters the burr hole cap 21 through the slot 24 that is cut in the cylindrical portion 21C of the burr hole cap 21. Thus the distal end of the helix 22 can be joined to the connector 26 and deep electrode 28 before the burr hole cap 21 is placed in the burr hole 25 that is formed in the cranium. After the deep electrode 28 has been placed, the burr hole cap 21 can be inserted over the wire 20 and into the burr hole 25 so that the cylindrical portion 21C makes a snug fit into the burr hole 25. Before inserting the burr hole cap 21 into the burr hole 25, an adhesive filler can be placed into the burr hole 25 for stabilizing the position of the helical wire coil 22, the deep electrode 28 and the burr hole cap 21.

Figure 5:
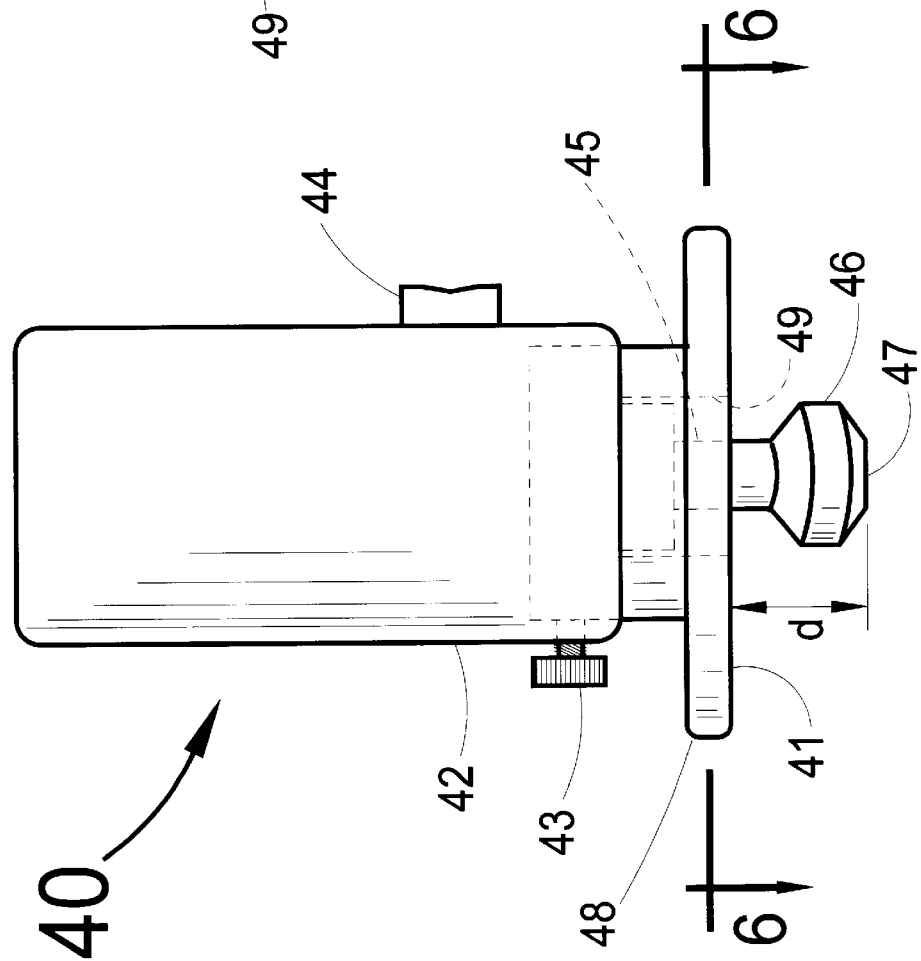
FIG. 5 is a side view of the cranial router.

FIG. 5 is a side view of a battery operated electrical router system 40 that includes a router driving portion 42, an ON-OFF switch 44, a router bit 46 having a shaft 45, and a depth limiter 48 with a depth adjustment screw 43 that adjusts the depth of the cut in the cranium made by router system 40 to a depth "d" as shown in FIGS. 2 and 5. That is, the depth of cut of the router system 40 is determined by the distance from the bottom surface 41 of the depth limiter 48 to the bottom surface 47 of the router bit 46. Thus, the bit 46 will form the desired shape and depth of the groove 20 as shown in FIG. 2. The typical depth "d" of the groove 20 would be between 0.5 and 3.0 millimeters.

Figure 6:
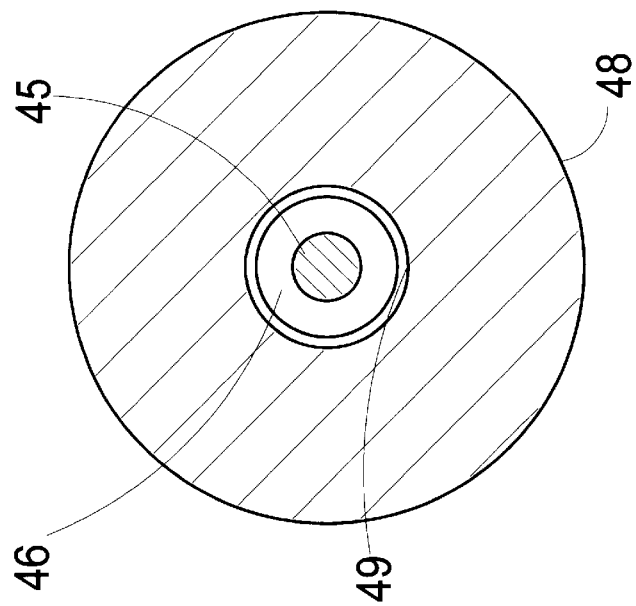
FIG. 6 is a cross section of the router at section 6—6 of FIG. 5 showing a cross section of the depth limiter and the router bit.

FIG. 6 is a cross section of the depth limiter 48 which has an inner hole 49 whose diameter is larger than the maximum diameter of the bit 46 so that router bits can be replaced between each procedure for different patients.

The method for placement of the intracranial system 10 would be as follows:

(a) Perform a surgical procedure to expose the cranium.

(b) Remove bone from the cranium to form a hole into which a control module with attached wires can be placed.

(c) Drill one or more burr holes in the cranium at the site(s) where a brain electrode is to be implanted.

(d) Use a router to form one or more grooves in the cranium, which grooves connect the control module to each burr hole.

(e) Place a control module with fixed lengths of wires into the hole in the cranium formed for the control module, at least some of the wires having a brain electrode located at the wire's distal end.

(f) Place one wire into each of the grooves formed by the router system.

(g) Place the distal portion of each wire into a burr hole, the distal portion of the wire being in the form of a helical coil.

(h) Place each brain electrode at an appropriate location.

(i) Place a burr hole cap into each burr hole.

Additionally, the steps of filling the burr holes or the grooves with an adhesive filler could also be accomplished. Also, it should be noted that the step of placing the burr hole cap into each burr hole could be avoided if an adhesive filler is placed in the burr hole.

It should be noted that although the control module is shown implanted within the cranium, other locations for placement of the control module such as under the scalp or in the patient's chest are also envisioned.

Various other modifications, adaptations, and alternative designs are of course possible in light of the above teachings. Therefore, it should be understood at this time that within the scope of the appended claims the invention may be practiced otherwise than as specifically described herein.

What is claimed is:

1. A system for electrically connecting an implantable control module to brain electrodes, the system comprising:

at least one brain electrode adapted to be placed onto, within or in close proximity to the brain;

a control module adapted to be implanted within a human subject; and an electrical wire joining each of the at least one electrodes to the control module, the electrical wire having a proximal portion, a distal portion and a distal end, the proximal portion being generally straight and the distal portion being formed into a helical coil, and the distal end of the electrical wire being attached to the brain electrode.

2. The system of claim 1 wherein there are at least two brain electrodes.

3. The system of claim 1 wherein the helical coil is adapted to be placed inside a burr hole within the cranium, the outside diameter of the helical coil being less than 2.5 centimeters so as to be able to be placed within a burr hole that is less than 2.5 centimeters in diameter.

4. The system of claim 3 wherein a burr hole cap having a disk-shaped top is adapted to be placed into the burr hole.

5. The system of claim 4 wherein the burr hole cap has a cylindrical portion connected to the disk-shaped top which cylindrical portion is adapted to be placed in the burr hole.

6. The system of claim 5 wherein the burr hole cap has a side hole in its cylindrical portion through which the electrical wire can be placed.

7. The system of claim 5 wherein the burr hole cap has a slot cut into the cylindrical portion so that the burr hole cap can be placed into the burr hole after the helical coil has been placed in the burr hole.

8. A method for the placement of brain electrodes beneath the scalp of a human patient, the method comprising:

(a) performing a surgical procedure to expose the cranium, (b) removing bone from the cranium to form a hole into which a control module with attached wires can be placed, (c) drilling one or more burr holes in the cranium at the site(s) where a brain electrode is to be implanted, (d) using a router to form one or more grooves in the cranium, which grooves connect the control module hole to each burr hole, (e) placing a control module with fixed lengths of wires into the hole in the cranium formed for the control module, at least some of the wires having a brain electrode located at the wire's distal end, (f) placing one wire into each of the grooves formed by the router, (g) placing a distal portion of each wire into a burr hole, the distal portion of the wire being in the form of a helical coil, (h) placing each brain electrode at an appropriate location.

9. The method of claim 8 including the filling of each burr hole with a filler material.

10. The method of claim 8 including placing a burr hole cap onto at least one burr hole.

11. The method of claim 8 including the filling of the one or more grooves with a filler material.

* * * * *